United States Patent [19]

Sanz et al.

[11] 3,996,001
[45] Dec. 7, 1976

[54] METHOD OF AND DEVICE FOR THE ANALYSIS OF LIQUIDS

[75] Inventors: Manuel Sanz, Grand-Lancy; Georges Revillet, Onex, both of Switzerland

[73] Assignee: Battelle Memorial Institute, Carouge, Switzerland

[22] Filed: May 12, 1975
(Under Rule 47)

[21] Appl. No.: 576,306

[30] Foreign Application Priority Data
May 10, 1974  Switzerland .................... 6391/74

[52] U.S. Cl. ........................ 23/230 R; 23/253 R; 23/259; 141/241; 141/325
[51] Int. Cl.² ................. G01N 31/00; G01N 31/22; G01N 33/16; B65B 3/04
[58] Field of Search .......... 23/230 R, 259, 292, 23/253 R; 141/241, 325

[56] References Cited
UNITED STATES PATENTS

| | | | |
|---|---|---|---|
| 3,692,486 | 9/1972 | Glenn | 23/253 R X |
| 3,841,765 | 10/1974 | Lambert et al. | 23/259 X |
| 3,873,271 | 3/1975 | Young et al. | 23/230 R X |
| 3,877,877 | 4/1975 | Prosen | 23/259 |
| 3,895,661 | 7/1975 | Praglin et al. | 23/259 X |

Primary Examiner—Norman Yudkoff
Assistant Examiner—Barry I. Hollander
Attorney, Agent, or Firm—Karl F. Ross; Herbert Dubno

[57] ABSTRACT

An improved device and method for liquid storage and analysis. The device comprises a receptacle defining a U-shaped compartment for a first open-ended branch and a second closed branch. A reaction zone in which the liquid will react with a reagent during analysis is located at the bight interconnecting the branches. The opening in the first branch constitutes a liquid inlet. A wall portion of the second branch spaced from the reaction zone is of self-sealing material which is punctured to release gas from the compartment and to aspirate liquid into the first branch. The material subsequently forms a fluid-tight seal. A wall portion of the body adjacent the reaction zone is made of light-permeable material so that the reaction or the result of the reaction can be optically analyzed. A plurality of such compartments can be provided with a chamber interconnecting the extreme ends of the second branches. A common wall portion of self-sealing material can then be provided for some or all of the compartments.

13 Claims, 6 Drawing Figures

METHOD OF AND DEVICE FOR THE ANALYSIS OF LIQUIDS

FIELD OF THE INVENTION

The present invention relates to the storage and analysis of a liquid. More particularly this invention concerns a device for reacting a liquid with a reagent.

BACKGROUND OF THE INVENTION

It is known that, in the field of medicine intended for the diagnosing of specific maladies, as in a hospital, it is required to analyze considerable numbers of samples in such manner that analysis by medical technicians is no longer readily available in view of labor costs and also in view of lack of qualified personnel.

There have already been proposed a number of devices permitting the analysis of a plurality of liquid samples. Known are, for example, devices comprising a plurality of compartments each of which contains a reagent appropriate for the analysis which it is desired to effect and into which the liquid to be analyzed is introduced successively with the aid of, for example, a pipette. The non-simultaneous introduction of the liquid into the various compartments has, however, the consequence that the reactions taking place in each compartment start at different instants, corresponding to the contacting of the liquid and the reagent, in such manner that, since the reaction commences immediately, "grouping" of a series of analyses to effect processing thereof with the aid of an automatic device, for example, is practically impossible.

The problem involved in simultaneity in respect of initiation of the reactions is partly solved by devices of the type described in German published patent application (Offenlegungschrift) No. 2,347,173 published April 18, 1974 which comprises a chamber in which the liquid to be analyzed is stored, a plurality of compartments each containing an appropriate reagent, and means for effecting simultaneous flow of the liquid to be analyzed from the chamber into each of the compartments. This means is for example a plurality of check valves or diaphragms rendered permeable due to application of a pressure difference. However, the presence of such means contributes to complicating these devices.

There is also known from German published patent application (Auslegeschrift) No. 2,028,822 published August 7, 1969 a liquid analysis device comprising a plurality of tubular compartments each divided by transverse diaphragms into a plurality of superposed chambers, each of the chambers containing an appropriate pre-stored reagent or solvent, and the compartments or containers being connected together at their lower portion in such manner as to form a common chamber. The liquid to be analyzed is introduced through the upper aperture of one of the compartments, whereas the transverse diaphragms are successively perforated in such manner as to permit the reaction to commence, the reaction products then falling into the lower common chamber where the analysis itself is effected by optical means. Such a device, apart from its complicated aspect, permits only one single analysis at a time on the sample.

OBJECTS OF THE INVENTION

It is therefore an object of the present invention to provide an improved device for analyzing a liquid.

Another object is the provision of an improved method of analyzing a liquid, or conducting a plurality of analyses of a liquid such as urine or blood.

Yet another object is to provide an improved system of the above-mentioned general type which is easy to use and can be adapted for use with automated optical analysis systems.

A further object is a liquid receptacle which is inexpensive to manufacture and usable for conducting analysis of a liquid.

Another object of the present invention is to provide a liquid analysis system which overcomes the afore-given disadvantages.

SUMMARY OF THE INVENTION

According to the present invention there is provided a device for stocking or storing a liquid and for analyzing this liquid, comprising a generally U-shaped receptacle having a pair of branches. The free end of one of the branches is formed with a liquid admission aperture and at least a portion of the bight located near the bottom of the U of the compartment contains a reagent and constitutes a reaction zone. The free end of the other branch is sealed with at least a portion of the wall of this other limb in the vicinity of its free end being made from self-sealing material. At least two portions of the wall of the compartment delimiting the reaction zone and located opposite each other are made as windows from a material which is permeable to light rays.

The present invention also includes a method of using the device wherein the admission or inlet aperture of the U-shaped compartment is contacted with or dipped into the liquid to be analyzed and there is then set up, within the compartment, a degree of negative pressure sufficient to permit aspiration of a portion of the liquid into at least part of the branch formed with the inlet aperture, this part then serving as storage zone. When it is desired to proceed to analysis of the liquid charge, the other branch is put into communication with the external atmosphere by piercing of the seal in such manner as to permit the escape of the gas entrapped in the compartment and to enable gravity to cause the liquid portion to flow gravitationally down into contact with the reagent. Then a ray or beam of light is passed through the windows so as to proceed by optical means to analysis of the reaction product thus obtained.

BRIEF DESCRIPTION OF THE DRAWING

The above and other objects, features, and advantages will become more readily apparent from the following description, reference being made to the accompanying drawing in which.

SPECIFIC DESCRIPTION

Figure 1C:
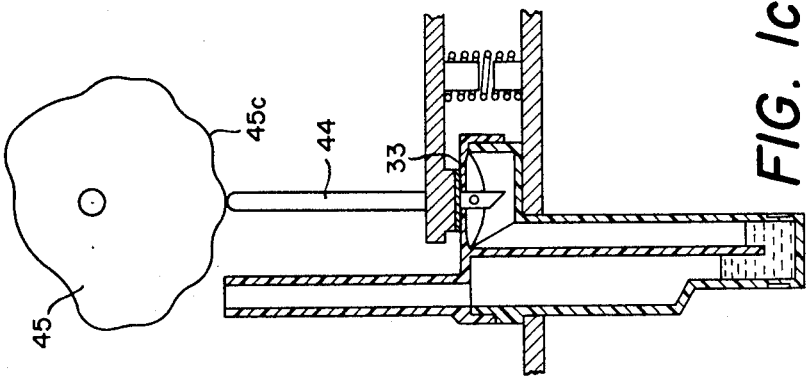
FIGS. 1a, 1b, and 1c are vertical sections through the device according to the present invention in different operational modes.

The receptacle shown in FIGS. 1a-c and 2 comprises two elements engaged in fluid-tight manner one within the other, i.e. upper and lower elements 7 and 8, respectively. The lower element 8 is constituted by a vessel which is open at its upper portion, has two parallel lateral faces 21 and 31, and is divided internally into a plurality of compartments 1 by vertical partitions 12 (FIG. 2) which are perpendicular to the lateral faces 21 and 31.

The partitions 12 are intersected by associated edges 12a located substantially at the commencement of a laterally projecting portion 8a of the container 8, in such manner as to form a duct 32 for communication between the compartments 1. The walls of the container closing the two ends of the ducts 32 each have an aperture or cutout 32a the purpose of which will be explained below.

Figure 2:
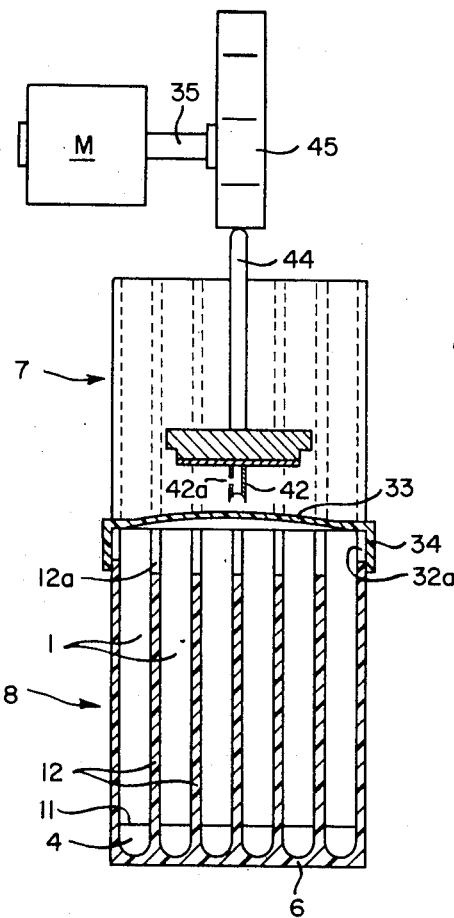
FIG. 2 is a section taken along line II—II of FIG. 1a, FIG. 3 is a longitudinal section through a syringe for piercing the seal of the apparatus of this invention.

As will be seen in FIG. 2, the bottom 6 of each of the compartments 1 is advantageously of semi-cylindrical profile with an axis perpendicular to the faces 21 and 31.

The lower element 8 is manufactured by injection molding of a transparent synthetic-resin material, polystyrene or a polyacrylate for example.

The upper element 7 forms a cover or lid enclosing in fluid-tight manner the top of the lower element 8. The inner face of the cover is formed with a row of tongues 11, lying in the same vertical plane and projecting downwardly in such manner that when the elements 7 and 8 are engaged one within the other each tongue 11 extends downwardly parallel to the lateral faces 21 and 31 to a location in proximity of the bottom 6 of the associated compartments 1, thus providing a passage or bight 4 between the free end of the tongue 11 and the bottom 6 of the compartment. The lateral edges of the tongues 11 are in fluid-tight contact with the partitions 12 so as to define within the associated compartments, two branches 2 and 3 connected to one another via the bight 4, the passage formed by the branch 2, the bight 4 and the branch 3 having the form of a U, and the upper portion of each of the branches 3 opening into the common duct 32.

The external face of the cover has two portions, the first located in line with the various branches 2, and the second in line with the various branches 3 of the compartments 1. The first portion, located opposite the limbs 2, projects vertically upwardly as a row of vertical tubular conduits 22 formed in this projecting portion of substantially square section and each extending directly above a respective branch 2, thereby establishing communication between the latter and the exterior. The second portion of the cover, located directly above or below the chambers 3 and covering the duct 32 and the projection 8a of the container 8, is constituted by a resilient diaphragm 33 whose purpose is explained below.

Figure 3:
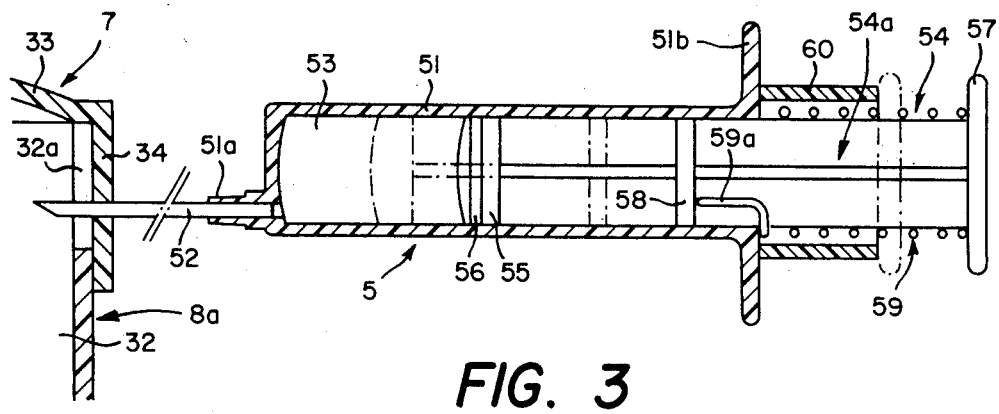

The upper element 7 also has an edge or flange 34 engaging tightly about the vessel 8, and descending to a location below the aperture 32a formed in the two ends of the duct 32 (FIGS. 2 and 3).

The upper element 7 is manufactured from a flexible and resilient material of the self-sealing type. The properties of this material and the wall thickness of the element 7 are such as to permit the passage of a perforating conduit, for example a syringe needle, through the wall and also withdrawal of this needle. On introduction into the passage 32 the perforating end of the conduit moves apart the material constituting the wall 34 and pierces a hole bounded by lips which bear in fluid-tight fashion against the conduit. The lips reclose against each other of their own accord in fluid-tight manner on withdrawal of the conduit. A synthetic-resin material such as polyvinyl chloride (PVC) may advantageously be used for this purpose.

Figure 1B:
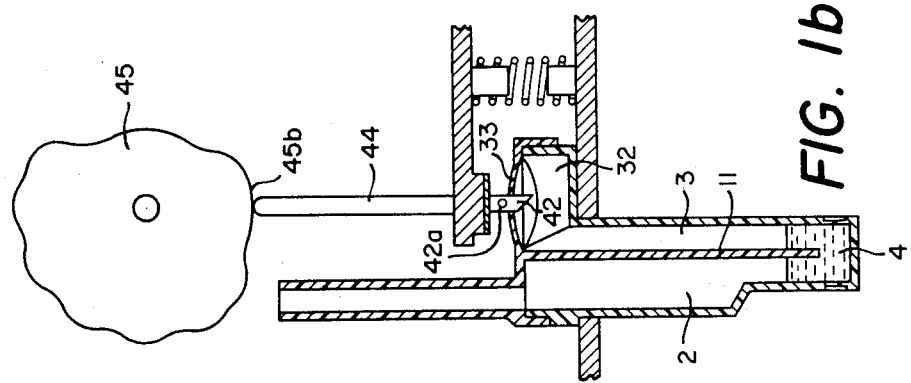
Figure 1A:
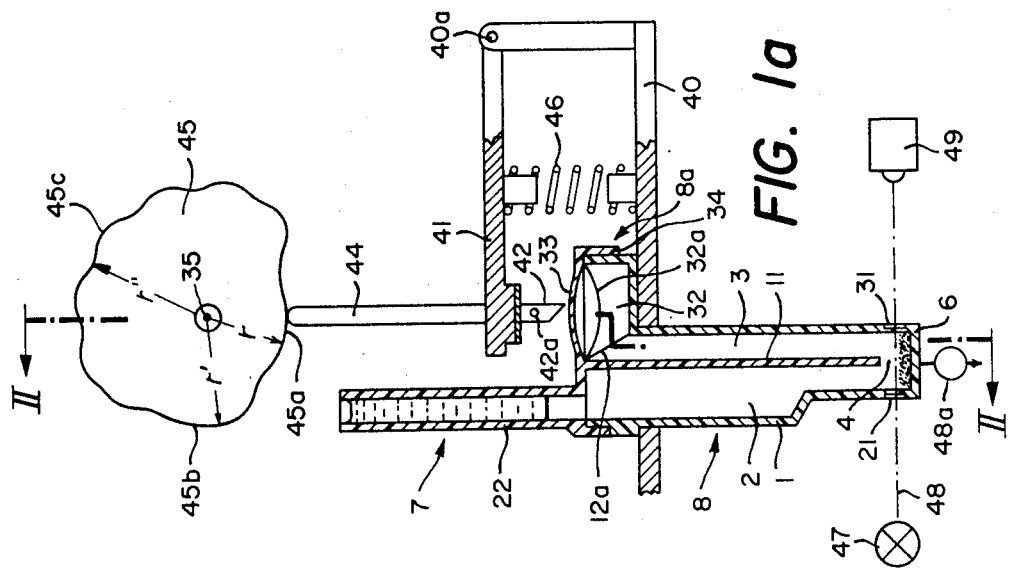

FIGS. 1a – 1c show furthermore a mechanism for operating the device described, and also a measurement device.

The operating mechanism comprises an arm 41 pivoted about a horizontal axle 40a fixed on a frame 40. The free end of the arm 41 carries a cam follower rod 44 extending upwardly and continuously urged against the edge of a rotary cam 45 by a spring 46 compressed between the frame 40 and the arm 41. The cam 45 is fixed on a shaft 35 of a motor M (FIG. 2).

The free end of the arm 41 carries, furthermore, a hollow lancet 42 extending in line with the rod 44, the lancet 42 being designed to face the diaphragm 33 in the raised position of the arm 41. A passage 42a extends from the tip of the lancet 42 and substantially halfway up the latter to a lateral outlet.

The profile of the cam 45 comprises a first section having the shape of a circular arc 45a, a second circular arc 45b the radius $r'$ of which is larger than the radius $r$ of the first, and a third section 45c comprising bumps wherein the radial distance $r''$ between the valleys and the axis of the cam is greater than the radius $r'$. The part played by these various sections will be explained later.

The optical measuring device comprises a battery of monochromatic light sources 47 (one of which is shown in FIG. 1a) and also a battery of photoreceivers 49 (one of which is shown in the same Figure) disposed, respectively, on either side of the transparent windows of faces 21 and 31, in such manner that a beam of light 48 emitted by the source 47 travels through the lower portion of each compartment below the respective tongue 11.

Photoreceiver cells 48a may also be disposed opposite the bottom 6 of the associated compartments, in particular with a view to analyzing a secondary beam the origin of which will be explained below.

A syringe 5 shown in FIG. 3, the purpose of which will be explained below, comprises a hollow cylinder 51 from the left-hand end of which projects a tubular element 51a; disposed in the aperture of this element is a needle 52. A plunger 54 is mounted for sliding within the cylinder 51. The open end of the cylinder is surrounded by a collar 51b.

The plunger 54 is constituted by two discs 55 and 58 fixed spaced apart on a cruciform frame 54a. The edge of the disc 55 is formed with an annular groove in which is disposed an O-ring packing 56, made for example of rubber or synthetic resin material.

The right-hand end of the plunger 54 has a pusher member 57 comprised of a disc the diameter of which is larger than that of the cylinder aperture.

A coil spring 59, surrounding the frame 54a, is compressed between the disc 58 and the pusher member 57. As will be seen in the drawings, the left-hand end of the spring 59 has a finger 59a extending parallel to the axis of the plunger 54 in the interior of the cylinder 5. The turn of the spring adjacent the finger bears against the collar 51b. A tubular ring 60 surrounds the plunger 54 over at least a portion of the projecting portion thereof; it is the object of the ring to limit the travel of the plunger 54 within the cylinder 51.

When it is desired to analyze a liquid, a reagent is introduced into the bight 4 of each container 1 of the device. A different reagent is usually used in each container. The reagents may be in any appropriate form, and notably in solid or powdered form, for example lyophilised. In a variant, it is of course possible to make use of a device wherein the reagents have been disposed at the bottom of each compartment at the factory, i.e. immediately subsequent to manufacture of the compartment itself.

Figure 4:
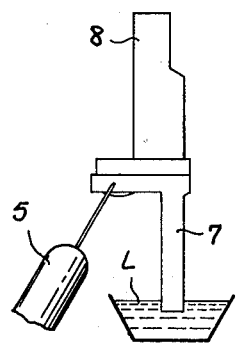
FIG. 4 is a small-scale perspective view illustrating use of the apparatus according to the present invention.

Then as shown in FIGS. 3 and 4, the needle of the syringe 5 is pricked through the edge of flange 34 of the cover 7, opposite one of the two recesses formed respectively in each end of the duct 32. A portion of the air contained in the syringe is expelled to the exterior through the tubular conduits 22, by exerting pressure on the pusher member 57 (shown in broken line) of the plunger. Then, the tubular conduits 22 are introduced into the liquid L to be analyzed (FIG. 4), while maintaining the pressure exerted on the pusher member. As soon as the pressure is released, the spring 59 urges the piston 54 into the position shown in solid lines, in such manner that substantially identical volumes of liquid are then sucked into each of the tubular conduits 22. The suction continues until the disc 58 abuts against the finger 59a of the spring 59.

The device is then inverted as illustrated in FIG. 1a, i.e. the position wherein the tubular conduits 22 are directed upwardly, and the needle 52 is extracted from the device. The wall 34, which is made from a flexible and resilient material, closes of its own accord, and since the air in the different compartments is trapped, the columns of liquids sucked into the tubular conduits are not able to descend into their associated compartments. Thus, they may be stored or stocked in this position for any time which may be required.

When it is desired to proceed to analysis of the liquid aspirated, the device is firstly fitted into the frame 40 of the actuation mechanism (FIG. 1a). The motor M is at a standstill and the articulated arm 41 in the raised position, the rod 44 being in contact with the section 45a of the cam 45, and the lancet 42 above the diaphragm 33.

Then the motor M is set in motion, thereby producing a downward movement of the articulated arm 41 with the rod means 44 in contact with the portion 45b of the edge of the cam 45. It follows that the lancet 42 (FIG. 1b) perforates the diaphragm 33 and penetrates through the latter to such an extent that the lateral outlet of the passage 42a remains located externally of the device.

It follows that the air trapped in the branches 2 and 3 of the device is able to escape, so that the liquid stored in the various conduits 22 falls to the bottom of the associated compartments and contacts the various reagents.

The positioning of the orifice for evacuation of the air trapped at the end of one of the branches 3 of the U constituted by the assembly comprising the tubular conduit 22, the branch 2, the bight 4, the branch 3, and completely opposite the liquid storage zone, permits the liquid to push all the trapped air in front of it, during its descent, and to fall freely as far as the bottom of the associated compartments. Any possibility of blocking of the liquid during its descent due to plugs constituted by residual air which might be produced between the storage zone and the bottom of the compartments is thereby prevented.

Since the motor continues to rotate, the rod 44 is subjected to the thrust of the edge of the corrugated section 45c of the cam 45 which follows the arc of a circle section 45b. Due to the fact that the minimum distance from the axis of this section 45c is greater than the radius of the arc of the section 45b, arrival on the end of the rod 44 on the section 45c has initially the effect of pushing the arm 41 further down, this movement ensuring penetration of the outlet of the orifice 42a of the lancet 42 under the diaphragm 33 and contacting of the arm 41 with the diaphragm 33 (FIG. 1c). Then, the successive passage of the rod 44 over the bumps constituting the edge of the corrugated section 35c has the effect of imparting oscillatory movement to the end of the articulated arm 41, while maintaining the end pressed against the diaphragm 33, in such manner that this oscillating movement is transmitted to the diaphragm. The diaphragm 33 thus acts as a pump produces a continuous reciprocating movement of the liquid through the bight 4 connecting the branches 2 and 3. This liquid mixing and agitation results in complete dissolving of the reagents, the homogenization of the solutions and the evacuation of any gas bubbles which might form on the lateral faces 21 and 31 of the containers, such bubbles possibly being caused for example due to an increase in temperature effected to obtain a given reaction.

The motor M is then stopped and analysis of the mixture which the device contains in each compartment is effected for example by colorimetry and with the aid of the photocells 49.

As a variant, it is also possible to analyze with the cell 48a the secondary radiation emitted by fluorescence of the liquid, disposed opposite the end faces 6 of the various compartments.

The device and the mode of functioning described hereinabove may comprise numerous variants which would not exceed the general scope of the invention. For example, it is possible to employ, instead of a syringe, any other device permitting the liquid to be aspirated. It is also possible while reacting and homogenizing the liquid to replace the actuating mechanism with any other device which would fulfill the same function; in particular, it is possible to effect the alternating pumping which gives rise to mising and agitation of the liquid by means of the syringe 5 by applying on the pusher member thereof a succession of pressures followed by releases.

In a further variant, wherein the temperature of the liquid located at the bottom of the various compartments is increased, for example with the aid of a heater in order to promote the reaction, the central portion of the diaphragm of the storage and analysis device advantageously is of decreased thickness, in such manner that any perforating element is readily able to tear a permanent hole in the central portion of the diaphragm. The downward movement of the actuation device then perforates this central portion, establishing communication between the common duct and the ambient air and giving rise to gravitational descent of the liquid columns. The downward continuation of this movement of the actuation device then provides for the alternating pumping, the end of the articulated arm passing into fluid-tight contact with the diaphragm. After the pumping, lifting of the articulated arm restores communication between the common duct and the ambient air. It is then possible to increase the temperature of the liquid contained at the bottom of the compartments without disturbing the equilibrium thereof, the two branches of each of the compartments being in communication with the hot ambient air.

It is also possible to precharge the tubular conduits 22 with various resins, with which the liquid columns will remain in contact during the entire period of sampling and storage.

The device according to the invention is suitable for application to numerous fields, notably chemistry and, more advantageously, the medical field, wherein it is required frequently and on a large scale to analyze blood, urine, or other biological liquids.

We claim:

1. A method of testing a liquid with a reagent in a receptacle having a U-shaped passage comprising a pair of branches joined together at a bight in which is provided said reagent, said method comprising the step of:
    dipping one end of one of said branches in a body of said liquid and withdrawing gas from the other branch to aspirate a portion of said liquid into said one branch;
    thereafter preventing gas escape from the other of said branches and positioning said receptacle with said portion of liquid above said bight;
    thereafter permitting gas to escape from said other branch and flowing said liquid gravitationally down said other branch into said bight and there reacting said liquid with said reagent; and
    thereafter passing light through said receptacle and said liquid and reagent at said bight to analyze the reaction between said reagent and said liquid.

2. The method defined in claim 1 wherein said gas is withdrawn from said other branch by piercing a hollow needle connected to means for producing suction through a wall of self-sealing material of said other branch.

3. The method defined in claim 2, further comprising the step of withdrawing said needle from said wall and sealing the hole formed therein by said needle, and varying the volume of said other branch after flowing of said liquid down into said bight to mix said liquid and reagent by pump action.

4. The method defined in claim 1 wherein said reaction is analyzed colorimetrically.

5. A method of testing a liquid with a reagent in a U-shaped receptacle having a pair of branches joined together at a bight in which is provided said reagent, said method comprising the step of:
    dipping one end of one of said branches in a body of said liquid and withdrawing gas from the other branch to aspirate a portion of said liquid into said one branch;
    thereafter preventing gas escape from the other of said branches and positioning said receptacle with said portion of liquid being retained by trapped gas in said receptacle above said bight;
    thereafter venting gas from said other branch and thereby causing said liquid to flow gravitationally down said other branch into said bight and there reacting said liquid with said reagent;
    thereafter passing light through said receptacle and said liquid and reagent at said bight to analyze the reaction between said reagent and said liquid, said gas being vented from said other branch by piercing a hollow needle through a wall of self-sealing material of said other branch; and
    mixing said liquid with said reagent by deflecting said wall.

6. An apparatus for reacting a liquid with at least one reagent, said apparatus comprising:
    a receptacle having a U-shaped passage, said passage comprising a bight and a pair of side-by-side branches codirectionally extending from said bight, said reagent being disposed in said bight, an end of one of said branches being open permanently to the atmosphere and forming a liquid storage compartment in which the liquid is held in place out of contact with said reagent by gas filling the remainder of said receptacle and prevented from escape therefrom when said compartment contains said liquid;
    a pair of light-permeable windows in said receptacle across from each other at said bight, whereby light can pass through said receptacle at said bight for analysis of the reaction of said liquid with said reagent; and
    a resilient elastic wall closing off the end of the other branch and formed at least partially of self-sealing elastic material, said wall being piercable to vent said gas from said receptacle to permit said liquid to contact said reagent, said wall being constructed and arranged so that its inward and outward deflection causes mixing of said liquid with said reagent.

7. The apparatus defined in claim 6 wherein said receptacle is formed with a plurality of such U-shaped passages and with a common duct interconnecting the end of the branches provided with said wall.

8. The apparatus defined in claim 7 wherein said duct is provided with said wall of self-sealing elastic material, whereby a syringe or the like can be pierced through said wall so as to withdraw gas from all of the closed-off branches simultaneously.

9. The apparatus defined in claim 8 wherein said receptacle is formed of a vessel having a plurality of concavities and of a cover tightly engaged over said vessel and having a plurality of tongues each forming in a respective concavity said U-shaped passage.

10. The apparatus defined in claim 9 wherein said cover is provided with a plurality of parallel tubes each registering with that branch of a respective passage that is not closed off.

11. The apparatus defined in claim 10 wherein said cover is entirely formed of said self-sealing material.

12. The apparatus defined in claim 11 wherein said vessel is made of light-permeable material of greater rigidity than said cover.

13. The apparatus defined in claim 12 wherein said cover is made of polyvinyl chloride and said vessel is made of polystyrene.

* * * * *

Dedication 3,996,001.—*Manuel Sanz*, Grand-Lancy and *Georges Revillet*, Onex, Switzerland. METHOD OF AND DEVICE FOR THE ANALYSIS OF LIQUIDS. Patent dated Dec. 7, 1976. Dedication filed Mar. 26, 1984, by the assignee, *Battelle Memorial Institute.*

Hereby dedicates to the People of the United States the entire remaining term of said patent.

[*Official Gazette May 22, 1984.*]